(12) United States Patent
Schraga (10) Patent No.: US 6,918,918 B1
(45) Date of Patent: Jul. 19, 2005

(54) SINGLE USE LANCET ASSEMBLY (76) Inventor: Steven Schraga, 9433 Byron Ave., Surfside, FL (US) 33154

( * ) Notice: Subject to any disclaimer, the term of this patent is extended or adjusted under 35 U.S.C. 154(b) by 178 days.

(21) Appl. No.: 10/134,996

(22) Filed: Apr. 29, 2002

Related U.S. Application Data
(60) Provisional application No. 60/312,196, filed on Aug. 14, 2001.

(51) Int. Cl.[7] ............................................... A61B 17/34
(52) U.S. Cl. ...................................................... 606/182
(58) Field of Search .............................. 606/181–185; 600/136, 137; 604/192, 197, 198

(56) References Cited

U.S. PATENT DOCUMENTS

| | | |
|---|---|---|
| 2,711,738 A | 6/1955 | Kelly et al. |
| 3,483,810 A | 12/1969 | Peters et al. |
| 3,906,626 A | 9/1975 | Riuli |
| 4,373,526 A | 2/1983 | Kling |
| 4,469,110 A | 9/1984 | Slama |
| 4,573,976 A | 3/1986 | Sampson et al. |
| 4,610,620 A | 9/1986 | Gray |
| 4,655,750 A | 4/1987 | Vaillancourt |
| 4,735,202 A | 4/1988 | Williams |
| 4,752,290 A | 6/1988 | Schramm |
| 4,758,231 A | 7/1988 | Haber et al. |
| 4,863,436 A | 9/1989 | Glick |
| 4,895,147 A * | 1/1990 | Bodicky et al. ............ 606/182 |
| 4,897,083 A | 1/1990 | Martell |
| 4,908,023 A | 3/1990 | Yuen |
| 4,944,736 A | 7/1990 | Holtz |
| 4,994,045 A | 2/1991 | Ranford |
| 4,994,068 A | 2/1991 | Hufnagle |
| 5,024,660 A | 6/1991 | McNaughton |
| 5,026,388 A | 6/1991 | Ingalz |
| 5,057,079 A | 10/1991 | Tiemann et al. |
| 5,088,996 A | 2/1992 | Kopfer et al. |
| 5,116,351 A | 5/1992 | Frassetti |
| 5,147,326 A | 9/1992 | Talonn et al. |
| 5,147,375 A | 9/1992 | Sullivan et al. |
| 5,160,326 A | 11/1992 | Talonn et al. |
| 5,181,609 A | 1/1993 | Spielmann et al. |
| 5,207,696 A | 5/1993 | Matwijcow |
| 5,219,333 A | 6/1993 | Sagstetter et al. |
| 5,222,945 A | 6/1993 | Basnight |
| 5,224,950 A | 7/1993 | Prywes |
| 5,241,969 A | 9/1993 | Carson et al. |
| 5,247,972 A | 9/1993 | Tetreault |
| 5,250,026 A | 10/1993 | Ehrlich et al. |
| 5,250,063 A | 10/1993 | Abidin et al. |
| 5,279,581 A | 1/1994 | Firth et al. |
| 5,297,599 A | 3/1994 | Bucheli |
| 5,304,136 A | 4/1994 | Erskine et al. |

(Continued)

FOREIGN PATENT DOCUMENTS

| | | |
|---|---|---|
| EP | 0 668 049 A1 | 8/1995 |
| EP | 0 894 471 A2 | 2/1999 |
| WO | WO 91/00215 | 1/1991 |
| WO | WO 00/78203 A2 | 12/2000 |

Primary Examiner—David Jacob Davis
(74) Attorney, Agent, or Firm—Malloy & Malloy, P.A.

(57) ABSTRACT

A single use lancet assembly having a housing, with an open interior and a piercing aperture defined therein, a lancet, with a body and a piercing tip positioned in the open interior of the housing and movable between a cocked orientation and a piercing orientation, a driving assembly structured to move the lancet into the piercing orientation, and a single use trigger assembly structured to actuate an actuating mechanism thereby allowing the lancet to move, at least temporarily, from its cocked orientation to its piercing orientation. The single use trigger assembly is structured such that it may not be positioned to actuate the actuating mechanism more than one time, thereby preventing inadvertent or intentional re-use of a contaminated piercing tip.

35 Claims, 4 Drawing Sheets

U.S. PATENT DOCUMENTS

| | | | |
|---|---|---|---|
| 5,304,192 | A | 4/1994 | Crouse |
| 5,312,347 | A | 5/1994 | Osborne et al. |
| 5,312,365 | A | 5/1994 | Firth et al. |
| 5,318,583 | A | 6/1994 | Rabenau et al. |
| 5,318,584 | A | 6/1994 | Lange et al. |
| 5,330,492 | A | 7/1994 | Haugen |
| 5,336,199 | A | 8/1994 | Castillo et al. |
| 5,346,480 | A | 9/1994 | Hess et al. |
| 5,350,392 | A | 9/1994 | Purcell et al. |
| 5,356,406 | A | 10/1994 | Schraga |
| 5,356,420 | A | 10/1994 | Czernecki et al. |
| 5,361,902 | A | 11/1994 | Abidin et al. |
| 5,395,388 | A | 3/1995 | Schraga |
| 5,417,662 | A | 5/1995 | Hjertman et al. |
| 5,423,847 | A | 6/1995 | Strong et al. |
| 5,439,473 | A | 8/1995 | Jorgensen |
| 5,454,828 | A | 10/1995 | Schraga |
| 5,462,535 | A | 10/1995 | Bonnichsen et al. |
| 5,464,418 | A | 11/1995 | Schraga |
| 5,468,233 | A | 11/1995 | Schraga |
| 5,469,964 | A | 11/1995 | Bailey |
| 5,487,748 | A | 1/1996 | Marshall et al. |
| 5,496,340 | A | 3/1996 | Abidin et al. |
| 5,501,672 | A | 3/1996 | Firth et al. |
| 5,518,004 | A | 5/1996 | Schraga |
| 5,527,334 | A | 6/1996 | Kanner et al. |
| 5,531,713 | A | 7/1996 | Mastronardi et al. |
| D376,203 | S | 12/1996 | Schraga |
| 5,584,846 | A | 12/1996 | Mawhirt et al. |
| 5,599,323 | A | 2/1997 | Bonnichsen et al. |
| 5,628,764 | A * | 5/1997 | Schraga ...................... 606/182 |
| 5,643,306 | A | 7/1997 | Schraga |
| 5,697,916 | A | 12/1997 | Schraga |
| 5,706,942 | A | 1/1998 | Vila et al. |
| 5,707,384 | A | 1/1998 | Kim |
| 5,730,753 | A | 3/1998 | Morita |
| 5,735,823 | A | 4/1998 | Berger |
| 5,738,665 | A | 4/1998 | Caizza et al. |
| 5,741,288 | A * | 4/1998 | Rife ........................... 606/181 |
| 5,746,761 | A | 5/1998 | Turchin |
| 5,755,733 | A | 5/1998 | Morita |
| 5,772,636 | A | 6/1998 | Brimhall et al. |
| 5,792,122 | A | 8/1998 | Brimhall et al. |
| 5,797,940 | A | 8/1998 | Mawhirt et al. |
| 5,797,942 | A | 8/1998 | Schraga |
| 5,836,920 | A | 11/1998 | Robertson |
| 5,868,771 | A | 2/1999 | Herbert et al. |
| 5,873,856 | A | 2/1999 | Hjertman et al. |
| 5,891,103 | A | 4/1999 | Burns |
| 5,908,434 | A * | 6/1999 | Schraga ...................... 606/181 |
| 5,947,934 | A | 9/1999 | Hansen et al. |
| 5,951,530 | A | 9/1999 | Steengaard et al. |
| 5,951,582 | A | 9/1999 | Thorne et al. |
| 5,954,738 | A | 9/1999 | LeVaughn et al. |
| 5,968,021 | A | 10/1999 | Ejlersen |
| 5,971,966 | A | 10/1999 | Lav |
| 5,980,491 | A | 11/1999 | Hansen |
| 5,984,906 | A | 11/1999 | Bonnichsen et al. |
| 6,015,397 | A | 1/2000 | Elson et al. |
| 6,022,366 | A | 2/2000 | Schraga |
| 6,050,977 | A | 4/2000 | Adams |
| 6,056,765 | A | 5/2000 | Bajaj et al. |
| 6,074,372 | A | 6/2000 | Hansen |
| 6,077,253 | A | 6/2000 | Cosme |
| 6,110,149 | A | 8/2000 | Klitgaard et al. |
| 6,149,608 | A | 11/2000 | Marshall et al. |
| 6,156,051 | A | 12/2000 | Schraga |
| 6,168,606 | B1 | 1/2001 | Levin et al. |
| 6,190,398 | B1 | 2/2001 | Schraga |
| 6,213,977 | B1 | 4/2001 | Hjertman et al. |
| 6,216,868 | B1 | 4/2001 | Rastegar et al. |
| 6,228,100 | B1 | 5/2001 | Schraga |
| 6,258,112 | B1 | 7/2001 | Schraga |
| 6,302,869 | B1 | 10/2001 | Klitgaard |
| 6,322,574 | B1 | 11/2001 | Lloyd et al. |
| 6,322,575 | B1 | 11/2001 | Schraga |
| 6,346,114 | B1 | 2/2002 | Schraga |
| 6,358,265 | B1 | 3/2002 | Thorne, Jr. et al. |
| 6,514,270 | B1 | 2/2003 | Schraga |
| 6,530,937 | B1 | 3/2003 | Schraga |

* cited by examiner

SINGLE USE LANCET ASSEMBLY

CLAIM OF PRIORITY

The present application is based on and a claim to priority is made under 35 U.S.C. Section 119(e) to provisional patent application currently pending in the U.S. Patent and Trademark Office having Serial No. 60/312,196 and a filing date of Aug. 14, 2001.

BACKGROUND OF THE INVENTION

1. Field of the Invention

The present invention relates to a single use lancet assembly which is substantially compact, yet effective for piercing a patient's finger or other body part to obtain a blood sample. The single use lancet device is further configured to be substantially safe, preventing re-use of the device after it has been actuated, by way of a single use trigger assembly that is structured to assure that subsequent use of a contaminated lancet tip cannot occur. Additionally, the assembly is cost effective and is fully disposable after a single use.

2. Description of the Related Art

Lancets are commonly utilized instruments which are employed both in hospitals and other medical facilities, as well as by private individuals, such as diabetics, in order to prick or pierce a patient's skin, typically on a finger of a patient, thereby leading to the generation of a blood sample which can be collected for testing. Because of the wide spread use of such lancets, there are a variety of lancet devices which are available for utilization by patients and/or practitioners in a variety of different circumstances.

For example, a typical lancet may merely include a housing with a sharp piercing tip that is pushed into the patient's skin. More commonly, however, lancet devices, which house a piercing tip and/or a lancet, have been developed which effectively encase and fire the lancet into the patient's skin, thereby eliminating the need for the person taking the sample to actually push the lancet tip into the skin.

Within the various types of specialized lancet devices, one variety are typically configured for multiple and/or repeated uses, while another category is particularly configured for single use, after which the entire device is disposed of. Looking in particular to the single use, disposable lancet devices, such devices typically include a housing which contains and directs or drives a piercing tip into the patient's skin, and which is disposed of along with the used lancet. Naturally, so to make such disposable devices cost effective for frequent use, such devices tend to be rather simplistic in nature providing only a sufficient mechanism for firing, and not overly complicating the design so as to minimize that cost.

While existing single use devices are generally effective for achieving the piercing of the skin required for effective operation, such single use, disposable devices typically do not incorporate a large number of safety features to assure the safe use and disposal of the device. For example, one primary area of safety which must be addressed with all lancet devices pertains to the purposeful and/or inadvertent reuse of a contaminated lancet. Unfortunately, most currently available single use lancet devices are configured such that after a use thereof has been achieved, it is possible for a patient to re-cock the device, thereby allowing for a subsequent, inappropriate use.

As a result, it would be highly beneficial to provide a single use lancet device which is substantially compact and disposable, can be manufactured in a substantially cost effective manner, and which nevertheless is substantially safe to utilize by affirmatively preventing re-use once contaminated. Additionally, while other devices may be provided which prevent a lancet from being re-cocked, it would be extremely desirable to provide an assembly which prevents re-use even if the assembly is re-cocked.

SUMMARY OF THE INVENTION

The present invention relates to a single use lancet assembly configured to pierce a patient's skin and is useable one time only, thereby preventing reuse of a contaminated lancet piercing tip. In particular, the present single use lancet assembly includes a housing having an open interior and a piercing aperture defined therein. The housing is preferably compact and includes a lancet disposed within its open interior.

Looking to the lancet, it is preferably of the type which includes a body and a piercing tip. It is the piercing tip which includes the pointed configuration structured to penetrate or pierce a patient's skin for the drawing of blood. Moreover, the lancet is cooperatively disposed within the open interior of the housing such that the lancet may move between at least a cocked orientation and a piercing orientation wherein the patient's skin is penetrated by the piercing tip.

Also operatively associated with the lancet is a driving assembly. The driving assembly is structured to move or drive the lancet, at least temporarily, into its piercing orientation from its cocked orientation. Preferably, however, the lancet assembly is configured such that the lancet is generally maintained in its cocked orientation until affirmatively released by a user. Along these lines, the single use lancet assembly of the present invention also includes a trigger assembly operatively associated with an actuating mechanism. The trigger assembly is disposed to be exteriorly actuatable from an exterior of the housing and is positionable to facilitate release of the actuating mechanism. When the lancet is in its cocked orientation, the actuating mechanism maintains the lancet in position until it is actuated, such as by pushing a portion of the actuating mechanism into the open interior of the housing and/or by disengaging the trigger assembly. When the lancet is released from its cocked orientation, the driving assembly propels the lancet at least temporarily into its piercing orientation wherein the piercing tip protrudes through the piercing aperture of the housing and, preferably, into the skin of the user.

In order to assure that the lancet assembly is used one time only, the trigger assembly of the present invention further preferably includes a trigger lock. The trigger lock is configured to prevent the trigger assembly from returning to an actuatable orientation after the trigger assembly has released the lancet from its cocked orientation. As such, by immobilizing the trigger assembly, re-use of the lancet is prevented thus assuring that inadvertent or intentional contact with a contaminated lancet by a user or another person does not occur.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown throughout the Figures, the present invention is directed towards a single use lancet assembly, generally indicated as 10. In particular, the single use lancet assembly 10 of the present invention includes a housing, generally indicated as 20. The housing 20 is preferably substantially small and compact, and may be made of one or a plurality of segments, preferably of a generally rigid, disposable material, such as plastic. The housing 20 includes an at least partially open interior 28 and at least one piercing aperture 22 defined therein. In addition, the lancet assembly 10 of the present invention also comprises a lancet, generally indicated as 30, In particular, the open interior 28 of the housing 20 is preferably sized and configured to effectively receive the lancet 30. The lancet 30 preferably includes a body 32 and a piercing tip 34. The piercing tip 34 is used to pierce a person's skin so as to draw blood to be utilized for a medical sample and/or test procedure. Moreover, the body 32 may be the shaft of the piercing tip 34 and/or an additional structure such as that depicted in the Figures. Regardless, however, the lancet 30 is structured to move within the open interior 28 of the housing 20, preferably at least between a cocked orientation, such as that depicted in the embodiment of FIG. 2, and a piercing orientation wherein the piercing tip 34 of the lancet 30 at least temporarily protrudes through the piercing aperture 22.

Figure 4:
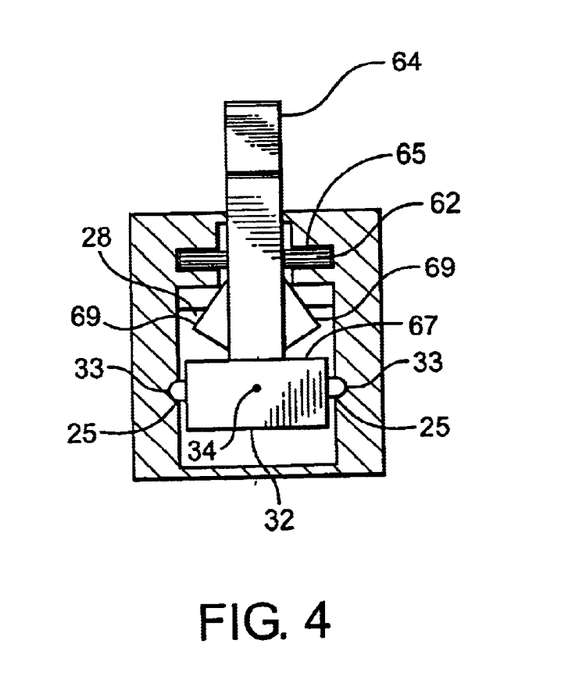
FIG. 4 is a front cross section view of the single use lancet assembly of FIG. 1 along 4—4 thereof.

Looking to FIG. 4, movement of the lancet 30 through the housing 20 is preferably maintained in a substantially linear path by a guide assembly. In the illustrated embodiment, the guide assembly includes at least one guide ridge 33 protruding from the body 32 of the lancet 30, and at least one corresponding guide track 25 structured to movably receive the guide ridge 33 therein. The guide track 25 preferably extends at least partially along a length of the open interior 28 of the housing 20 so as to maintain the guide ridge 33 effectively therein during a necessary range of motion of the lancet 30. As depicted in FIG. 4, preferably a pair of guide ridges 33 are disposed on opposite sides of the lancet body 32, with a corresponding pair of oppositely disposed guide tracks 25 being defined in the housing. It is of course, however, understood that the guide tracks 25 need not necessarily be directly defined in the housing 20, but may be defined by additional elements secured therein, and conversely the guide track (s) 25 may be defined in or on the lancet body 32, with the guide ridge(s) 33 extending inwardly from the housing 20.

Figure 1:
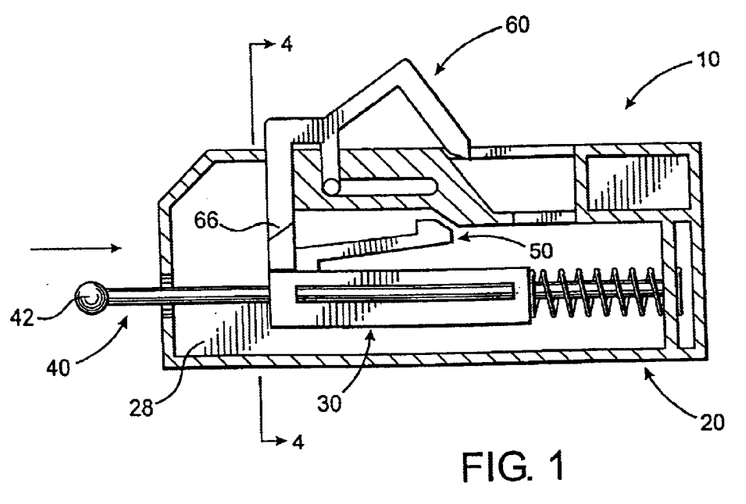
FIG. 1 is a side cross section view of one embodiment of the single use lancet assembly of the present invention in an unused, initially un-cocked orientation.

Looking in further detail to the illustrated lancet assembly 10, and the path of movement of the lancet 30 within the housing 20, when the lancet assembly 10 is initially obtained for use, the lancet 30 can be pre-cocked or maintained in an initially un-used and un-cocked orientation, as best seen in FIG. 1. In this initially un-used and un-cocked orientation a protective cover 40 may extend into the open interior 28 of the housing 20 so as to at least partially and removably cover the piercing tip 34 of the lancet 30, thereby maintaining the safety and sterility of the piercing tip 34 when not being used. In this regard, the protective cover 40 may be formed from a variety of preferably rigid materials and is structured to protrude from the housing 20. Furthermore, the protective cover 40 may include an enlarged head 42 configured to facilitate grasping thereof and may be molded with or separate from the remainder of the lancet.

Figure 2:
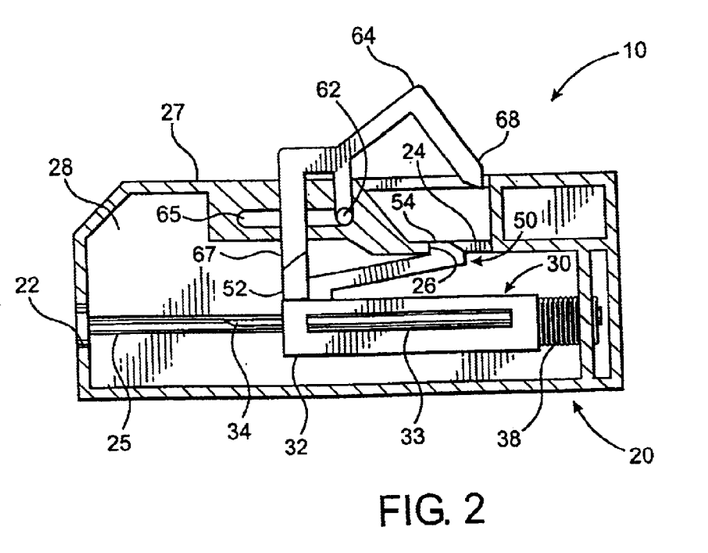
FIG. 2 is a side cross section view of the single use lancet assembly of FIG. 1 illustrating a cocked orientation.

In order to effectively retain, and subsequently release, the lancet 30 from its cocked orientation, the single use lancet 10 of the present invention further includes an actuating mechanism. A variety of different actuating mechanisms may be incorporated to effectively retain the lancet 30 in its cocked orientation, however, as illustrated in FIG. 2, one embodiment utilizes an actuating mechanism 50 which is secured, either directly or indirectly, to the lancet 30 and is also structured to engage at least a portion of the housing 20. In addition, the actuating mechanism 50 is actuatable permitting the release of a driving assembly 38 from a compressed orientation. As such, the actuating mechanism 50 of the present invention is structured to be both cocked and actuated, one time only, by a trigger assembly, generally shown as 60.

In a preferred embodiment of the present invention, the trigger assembly 60 is structured such that it can cock and actuate the actuating mechanism 50 one time only. Additionally, the trigger assembly 60 preferably includes a cocking member 67 which cooperatively associates with a cocking surface 52 of the actuating mechanism 50, wherein the cocking member 67 is structured to engage the cocking surface 52 and move the lancet 30 from its initial un-used orientation to its cocked orientation, as illustrated in FIG. 2, by selectively positioning a trigger 64. It is also recognized, however, that the cocking surface 52 may define the actuating mechanism 50, the lancet being maintained only momentarily cocked by the trigger assembly itself prior to release.

In the illustrated embodiment, the actuating mechanism so further includes an actuating surface 54 structured to be at least temporarily positioned into an actuation aperture 24 when the lancet 30 is in its cocked orientation. Furthermore, the actuating mechanism 50 is structured to generally restrict movement of the lancet 30 from its cocked orientation, at least partially defined by the actuating surface 54 positioned into the actuation aperture 24, effectively retaining the lancet 30 in its cocked orientation. Specifically, the actuating mechanism 50 extends from the body 32 of the lancet 30 along a biasing portion 56 terminating at the actuating surface 54, and at least a portion of the actuating mechanism 50 abuts an interior surface 26 of the housing 20 within the actuation aperture 24, thereby preventing movement of the lancet 30 from its cocked orientation, as illustrated in FIG. 2. When, however, the actuating mechanism 50 is actuated, for example, by pushing the actuating surface 54 down into the open interior 28 of the housing 20, the abutting engagement is released and the lancet 30 is permitted to freely move within the housing 20 into its piercing orientation, at least temporarily. As mentioned, although the preceding defines the illustrated actuating mechanism 50, it is understood that a variety of alternative actuating mechanisms 50, such as those including separate elements to retain and to release the lancet 30 may also be provided, and/or including structures which are actually part of the driving assembly 38, may also be provided.

In an alternate, less preferred embodiment of the present invention, the protective cover 40 may be structured to allow the user to move the lancet 30 into its cocked orientation by pushing the enlarged head 42 toward the housing 20, as depicted by the arrow in FIG. 1, thereby positioning the actuating surface 54 into the actuation aperture 24. Once in the cocked orientation, the protective cover 40 may be removed from the piercing tip 34, for example, by a twisting thereof, thereby leaving the piercing tip 34 completely exposed for use.

The single use lancet of the present invention further includes the driving assembly, generally indicated as 38. The driving assembly 38 is particularly configured to move the lancet 30 at least temporarily into its piercing orientation wherein the piercing tip 34 protrudes through the piercing aperture 22 of the housing 20 a desired amount. In particular, if desired, a depth adjustment structure could be positioned at the piercing aperture 22 to control the amount which the piercing tip protrudes from the housing 20. For example, a threaded washer type element could be adjustably secured to the housing 20 in generally surrounding relation to the piercing aperture 22.

Figure 3:
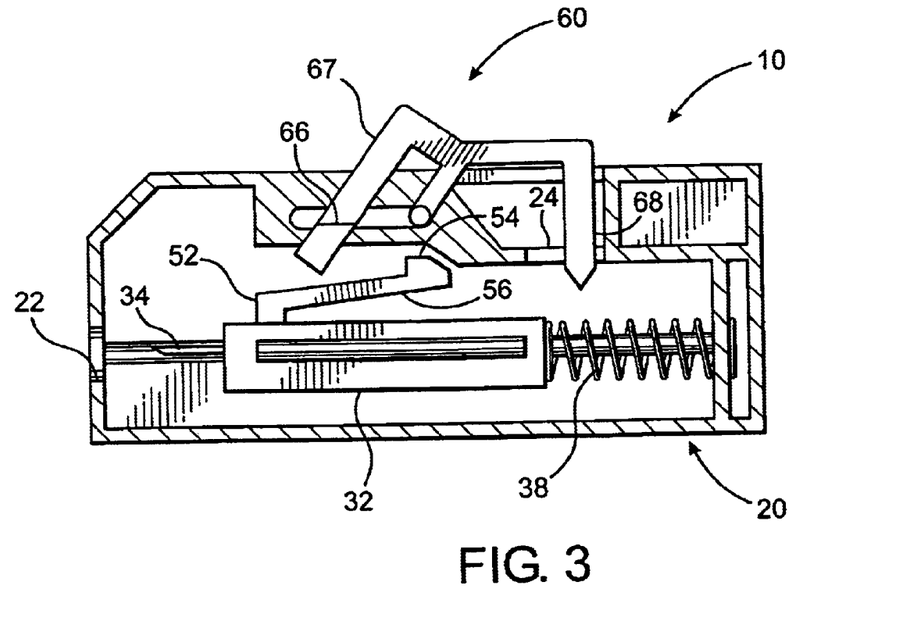
FIG. 3 is a side cross section view of the single use lancet assembly of FIG. 1 after movement into a piercing orientation from the cocked orientation.

Looking further to the driving assembly 38, preferably the driving movement occurs when the lancet 30 is released from its cocked orientation. In the illustrated embodiment, the driving assembly 38 includes a biasing element operatively disposed between the lancet 30 and the housing 20. Moreover, in the illustrated embodiment, a spring is preferably utilized as the biasing element, however, it is recognized that a variety of other driving assemblies may be utilized, including a wedge assembly, a hammer type assembly and/or a resilient material plate, segment or extension, all of which may be configured to move the lancet 30 from its cocked orientation into its piercing orientation. Further, it is preferred that based upon the size of the housing 20 and the nature and size of the driving assembly 38, that after the lancet 30 has moved into its piercing orientation wherein the piercing tip 34 at least temporarily protrudes through the piercing aperture 22, the lancet 30 tends to be retracted back into the housing 20, as best illustrated in FIG. 3. As a result, the used piercing tip 34 is effectively concealed within the housing 20 subsequent to usage, protecting against inadvertent or intentional engagement between the user or another person and the used piercing tip 34. Indeed, it is recognized that a second biasing element may be positioned in from of the lancet 30 so as to drive it back into the housing after it has passed into the piercing orientation.

As previously mentioned, the present invention preferably includes a single use trigger assembly 60 structured to both cock and actuate the actuating mechanism 50 one time only. The trigger assembly 60 is disposed to be exteriorly actuatable, and in the illustrated embodiments substantially on the exterior of the housing 20, and is positionable to facilitate cocking and subsequent actuation of the actuating mechanism 50, as illustrated throughout the Figures. In order to facilitate selective positioning of the trigger assembly 60, the present invention preferably comprises at least one trigger guide 62 which engages a pivot point of the trigger 64. In an alternate embodiment, a pair of trigger guides 62 may engage the pivot point of the trigger 64. The trigger guides 62 may be integral to the trigger 64 such as, by way of example only, tabs molded directly with or onto the trigger 64. Alternatively, the trigger guides 62 may be separate components, such as cylindrical axles which operatively engage the pivot point of the trigger 64. The trigger guides 62 are structured such that the trigger 64 is selectively and slidingly positionable along a trigger track 65 disposed on the housing 20. The trigger track 65 may be formed as an integral component of the housing 20, as illustrated throughout the Figures, or, in an alternate embodiment, the trigger track 65 may be a separate component mounted to an external surface 27 of the housing 20.

In order to actuate the trigger assembly 60, the actuation member 68 is positioned into alignment with the actuation aperture 24, such as while the lancet 30 is in its cocked orientation as in the embodiment of FIG. 2, or merely when the trigger assembly 60, and therefore the lancet 30 in the case of the illustrated embodiments, have been sufficiently retracted. A rearward force is applied to the upwardly extending portion of the trigger 64 causing the actuation member 68 to move downward into engagement with the actuating surface 54 pushing the actuating mechanism 50 into the open interior 28 of the housing 20, thereby permitting the driving assembly 38 to move the lancet 30, at least temporarily, from its cocked orientation into its piercing orientation and/or releasing the engagement by the trigger assembly.

In order to assure that the lancet assembly 10 of the present invention is used one time only, the trigger assembly 60 further comprises a trigger lock 66. In one preferred embodiment, the trigger lock 66 is disposed along the cocking member 67 of the trigger assembly 60. Additionally, the trigger lock 66 comprises at least one, but preferably a pair of locking members 69 which are positioned along the sides of the cocking member 67 in an upwardly outward extending configuration, as illustrated in FIGS. 1 through 4. The locking members 69 are normally disposed in the open interior 28 of the housing 20 below the trigger track 65, prior to the actuation of the trigger assembly 60. However, upon actuation of the trigger assembly 60, the downward force applied to the trigger 64, as described above, pivots the trigger 64 along its pivot point thereby pulling the cocking member 67 upward and at least partially out of the housing 20, and consequently pulling the locking members 69 upward into the trigger track 65, as illustrated in FIG. 3. Due to the laterally outward extending configuration of the locking members 69, once they are positioned within the trigger track 65, the locking members 69 cannot be repositioned back into the open interior 28 of the housing 20, thereby preventing the cocking member 67 and the actuation member 68 from being returned to their respective pre-actuation orientations. In an alternative configuration, the locking members 69 may be disposed along the cocking member 67 such that upon actuation of the trigger assembly 60, the locking members 69 are pulled upward and completely out of the housing 20, wherein their laterally outward extending configuration prevents the cocking member 67 and the actuation member 68 from returning to their respective pre-actuation orientations.

Figure 5:
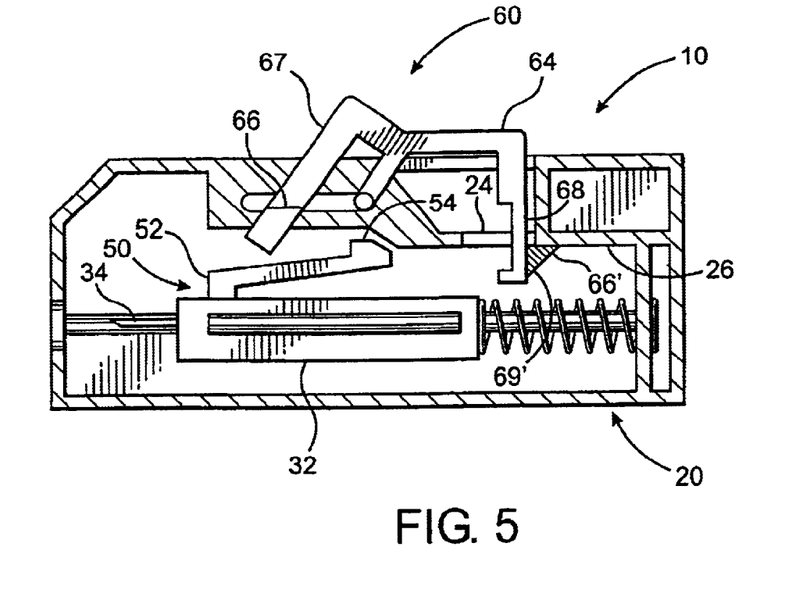
FIG. 5 is a side cross section view of an alternate embodiment of the single use lancet assembly of present invention after movement into a piercing orientation.

An alternate embodiment of the present invention includes a trigger lock 66' having a locking member 69' positioned along a rearward portion of the actuation member 68. The locking member 69' may comprise a generally wedge shape configuration, wherein upon positioning of the actuation member 68 into the actuation aperture 24, a portion of the locking member 69' engages an interior surface 26 of the housing 20, as illustrated in FIG. 5, thus preventing removal of the actuation member 68 from the open interior of the housing, thereby eliminating the possibility of re-actuation of the actuating mechanism 50. In one variation of this embodiment, the locking member 69' may be inwardly bailable while positioning the actuation member 68 through the actuation aperture 24, thereafter returning to a normally outwardly biased position engaging the interior surface 26 of the housing 20. In another variation of this embodiment, the locking member 69' may be structured to positively engage a notch or groove in the interior surface 26 of the housing 20.

Figure 6:
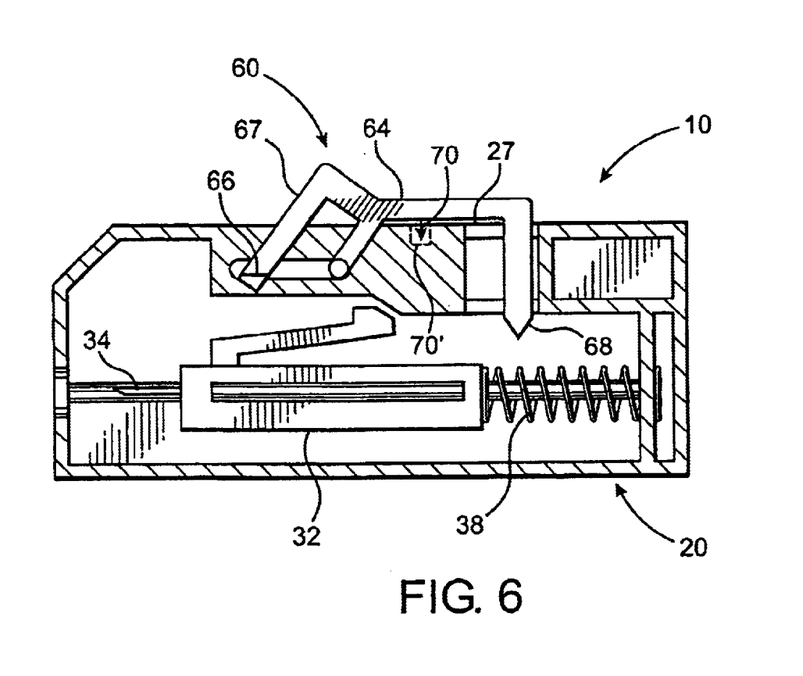
FIG. 6 is a side cross section view of yet another alternate embodiment of the single use lancet assembly of present invention after movement into a piercing orientation.

Yet another alternate embodiment of the present invention includes a first locking member 70 which is positioned on the underside of the trigger 64 between the actuation member 68 and the pivot point, facing the housing 20, as illustrated in FIG. 6. Upon actuation of the trigger assembly 60, the first locking member 70 operatively engages a second locking member 70' which is disposed on an exterior surface 27 of the housing 20 thereby immobilizing the trigger assembly 60 and preventing its movement into an actuating orientation. One of either the first locking member 70 or the second locking member 70' may be structured to be at least temporarily biased into a compressed configuration so as to permit entry through an aperture of the other member, thereafter returning to an unbiased, expanded configuration so as to prevent its removal from the aperture of the other member.

In addition to the trigger lock 66, once the actuation member 68 has been positioned through the actuation aperture 24, the actuation member 68 may prevent cocking of the lancet 30, even by manual utilization of the protective cover 40 as described above, due to the presence of the actuation member 68 in the actuation aperture 24. At least one embodiment of the present invention may comprise an actuation member 68 which is structured so as to allow the lancet 30 to be re-cocked after actuation, via a partially notched portion on the actuation member 68, as illustrated in FIG. 5. However, re-cocking the lancet 30 after actuation only serves to further assure that the used piercing tip 34 does not inadvertently or intentionally contact the user or another person by locking the lancet 30 in place within the housing 20, because it cannot be re-actuated since the trigger assembly 60 is locked and immobilized after only one use.

Figure 7:
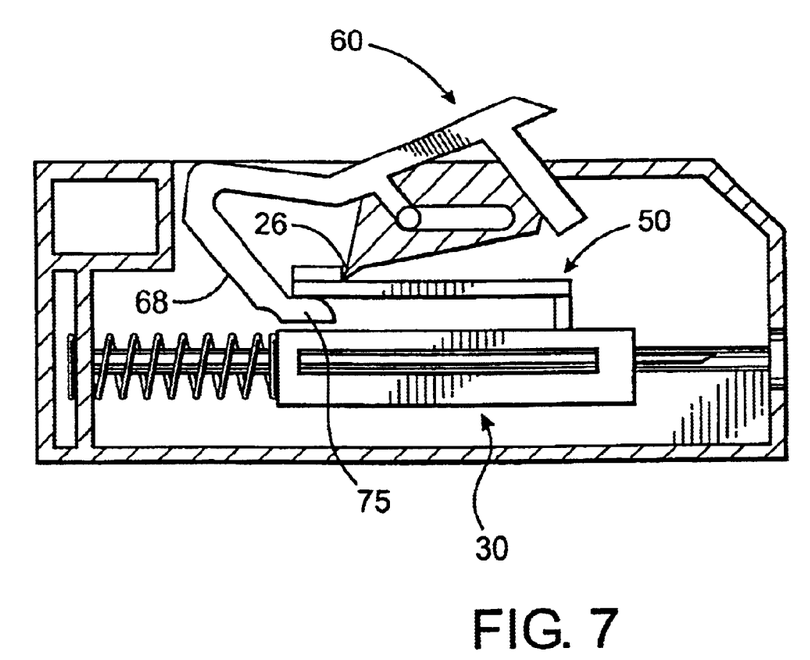
FIG. 7 is a side cross sectional view of an alternate, preferred embodiment of the single use lancet asset assembly of the present invention after movement into the piercing orientation.

Indeed, looking to a preferred embodiment of FIG. 7, the recessed region defined by the inwardly extending lip 75 on the actuation member 68 may serve to define a lock member and thereby the trigger lock. Specifically, the lip 75 may be configured to extend sufficiently inward such that after the lancet 30 has retracted from its piercing orientation, the actuating mechanism 50 will engage the lip 75 and prevent the actuation member 68 from being retracted so as to permit further actuation of the trigger assembly 60. Of course, in such an embodiment the actuation member 68 may or may not function to release lancet from its cocked orientation. Alternately, the angle of the actuation member 68 may be such that after it releases the lancet, a rotational movement thereof results in the lip 75 engaging the abutment surface 26, that engagement preventing movement of the trigger assembly 60 back into a pre-fired orientation.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. A single use lancet assembly comprising:
   a housing, said housing including an at least partially open interior and a piercing aperture defined therein;
   a lancet, said lancet including a body and a piercing tip;
   said lancet disposed in said open interior of said housing and structured to move at least between a cocked orientation and a piercing orientation;
   a trigger assembly structured to position said lancet into said cocked orientation and to release said lancet from its cocked orientation; and
   a driving assembly structured to move said lancet at least temporarily into said piercing orientation; and
   said trigger assembly further including a trigger lock structured to at least partially immobilize said trigger assembly within at least a portion of said housing after said lancet has been affirmatively released one time, thereby preventing repositioning of said trigger assembly to a pre-actuation orientation and preventing re-firing of said lancet.

2. A single use lancet as recited in claim 1 wherein said driving assembly includes a biasing element operatively disposed between said lancet and said housing.

3. A single use lancet as recited in claim 2 wherein said biasing element comprises a spring.

4. A single use lancet as recited in claim 1 wherein said trigger assembly is structured to at least, temporarily protrude from said housing when said lancet is disposed in said cocked orientation.

5. A single use lancet as recited in claim 1 further comprising an actuating mechanism structured to engage said lancet and abut an interior surface of said housing so as to retain said lancet in said cocked orientation until said lancet is affirmatively released.

6. A single use lancet as recited in claim 5 wherein said trigger assembly is structured to be at least partially immobilized after said lancet has been affirmatively released.

7. A single use lancet as recited in claim 1 wherein said trigger lock comprises at least one locking member connected to said trigger assembly and structured to engage said housing thereby preventing repositioning of said trigger assembly to a pre-actuation orientation after said lancet has been affirmatively released one time.

8. A single use lancet as recited in claim 1 wherein said trigger lock comprises at least one locking member connected to a cocking member of said trigger assembly and structured to engage a trigger track thereby preventing repositioning of said trigger assembly to a pre-actuation orientation after said lancet has been affirmatively released one time.

9. A single use lancet as recited in claim 1 wherein said trigger lock comprises a pair of locking members connected to a cocking member of said trigger assembly and structured to engage a trigger track thereby preventing repositioning of said trigger assembly to a pre-actuation orientation after said lancet has been affirmatively released one time.

10. A single use lancet as recited in claim 1 further comprising an actuating mechanism disposed between said lancet and said housing and structured to prevent said lancet from moving out of said cocked orientation until affirmatively released.

11. A single use lancet as recited in claim 10 wherein said actuating mechanism comprises an actuating surface and is further structured to abut an interior surface of said housing thereby preventing said lancet from moving out of said cocked orientation until affirmatively released.

12. A single use lancet as recited in claim 11 wherein said actuating mechanism comprises a biasing portion extending from said lancet.

13. A single use lancet as recited in claim 12 wherein said trigger assembly is structured to at least partially engage said actuating surface and push said actuating mechanism into said open interior of said housing thereby affirmatively releasing said lancet from said cocked orientation.

14. A single use lancet as recited in claim 10 wherein including a lock member structured to extend into said housing after actuation of said trigger assembly, said lock member structured to be engaged by said actuating mechanism so as to retain said trigger assembly in a post-actuation orientation and prevent re-firing of said lancet.

15. A single use lancet as recited in claim 14, wherein said lock member is structured to sufficiently receive said actuating mechanism so as to permit re-cocking of said lancet, said retention of said trigger assembly in said post actuation orientation preventing re-firing of said lancet.

16. A single use lancet as recited in claim 1 further comprising a guide assembly operatively disposed between said lancet and said housing and structured to maintain a substantially linear movement of said lancet through said housing.

17. A single use lancet as recited in claim 16 wherein said guide assembly comprises at least one guide ridge protruding from said body of said lancet, and at least one corresponding guide track structured to movably receive said guide ridge therein and extending at least partially along a length of said open interior of said housing.

18. A single use lancet as recited in claim 16 wherein said guide assembly comprises a pair of guide ridges protruding from said body of said lancet, and a pair of corresponding guide tracks structured to movably receive said guide ridges therein and extending at least partially along a length of said open interior of said housing.

19. A single use lancet as recited in claim 1 further comprising a protective cover structured to at least partially and removably cover said piercing tip of said lancet at least prior to movement of said lancet into said cocked orientation.

20. A single use lancet as recited in claim 19 wherein said protective cover is structured to protrude through said piercing aperture of said housing and is further structured to be pushed into said housing by a user so as to position said lancet into said cocked orientation.

21. A single use lancet assembly comprising:
a housing, said housing including an at least partially open interior and a piercing aperture defined therein;
a lancet, said lancet including a body and a piercing tip;
said lancet disposed in said open interior of said housing and structured to move at least between a cocked orientation and a piercing orientation;
a trigger assembly structured to at least position said lancet into said cocked orientation;
an actuating mechanism secured to said lancet and structured to abut an interior portion of said housing thereby retaining said lancet in said cocked orientation until affirmatively released;
said trigger assembly further structured to at least partially engage an actuating surface on said actuating mechanism and push said actuating mechanism into said open interior of said housing thereby affirmatively releasing said lancet from said cocked orientation; and
a driving assembly structured to move said lancet at least temporarily into said piercing orientation:
said trigger assembly including a trigger lock structured to at least partially immobilize said trigger assembly within at least a portion of said housing after said lancet has been affirmatively released one time thereby preventing repositioning of said trigger assembly to a pre-actuation orientation.

22. A single use lancet as recited in claim 21 wherein said trigger lock comprises at least one locking member connected to a cocking member of said trigger assembly structured to engage a trigger track thereby preventing repositioning of said trigger assembly to a pre-actuation orientation after said lancet has been affirmatively released one time.

23. A single use lancet as recited in claim 21 wherein said trigger lock comprises a pair of locking members connected to a cocking member of said trigger assembly structured to engage a trigger track thereby preventing repositioning of said trigger assembly to a pre-actuation orientation after said lancet has been affirmatively released one time.

24. A single use lancet as recited in claim 21 wherein said trigger lock comprises a lock member structured to extend into said housing and be engaged by said actuating mechanism after said lancet has moved into said piercing orientation, said actuating mechanism structured to retain said lock member and accordingly said trigger assembly in a post actuated orientation.

25. A single use lancet as recited in claim 21 further comprising a protective cover structured to at least partially and removably cover said piercing tip of said lancet at least prior to movement of said lancet into said cocked orientation.

26. A single use lancet as recited in claim 25 wherein said protective cover is structured to protrude from said piercing aperture of said housing and is structured to be pushed by a user so as to position said lancet into said cocked orientation.

27. A single use lancet as recited in claim 21 further comprising at least one guide ridge protruding from said body of said lancet, and at least one corresponding guide track structured to movably receive said guide ridge therein and extending at least partially along a length of said open interior of said housing.

28. A single use lancet as recited in claim 21 wherein said guide assembly comprises a pair of guide ridges protruding from said body of said lancet, and a pair of corresponding guide tracks structured to movably receive said guide ridges therein and extending at least partially along a length of said open interior of said housing.

29. A single use lancet assembly comprising:
a housing, said housing including an at least partially open interior and a piercing aperture defined therein;
a lancet, said lancet including a body and a piercing tip;
said lancet disposed in said open interior of said housing and structured to move at least between a cocked orientation and a piercing orientation;
a trigger assembly structured to at least position said lancet into said cocked orientation;
an actuating mechanism disposed at least partially in said housing and structured to retain said lancet in said cocked orientation until affirmatively released;
said trigger assembly further structured to engage and affirmatively release said actuating mechanism thereby affirmatively releasing said lancet from said cocked orientation;
a driving assembly structured to move said lancet at least temporarily into said piercing orientation; and
a trigger lock structured to at least partially immobilize said trigger assembly in at least a portion of said housing after said lancet has been affirmatively released one time thereby preventing repositioning of said trigger assembly to a pre-actuation orientation.

30. A single use lancet as recited in claim 29 wherein said lancet is structured to be re-cocked after movement thereof into said piercing orientation, said trigger lock being structured to prevent re-actuation of said trigger assembly and a subsequent release of said lancet from said cocked orientation.

31. A single use lancet as recited in claim 29 wherein said trigger lock comprises a pair of locking members connected to a cocking member of said trigger assembly and structured to engage a trigger track thereby preventing repositioning of said trigger assembly to a pre-actuation orientation after said lancet has been affirmatively released one time.

32. A single use lancet as recited in claim 29 wherein said trigger lock comprises a bailable locking member connected to an actuating member of said trigger assembly and structured to engage an interior surface of said housing thereby preventing repositioning of said trigger assembly to a pre-actuation orientation after said lancet has been affirmatively released one time.

33. A single use lancet as recited in claim 32 wherein said trigger lock comprises a lock member structured to extend into said housing and be engaged by said actuating mechanism after said lancet has moved into said piercing orientation, said actuating mechanism structured to retain said lock member and accordingly said trigger assembly in a post actuated orientation.

34. A single use lancet as recited in claim 29 wherein said trigger lock comprises a first locking member disposed on said trigger and a second locking member disposed on an exterior surface of said housing wherein said first and second locking members are structured to operatively engage one another upon affirmatively releasing said lancet one time and at least partially immobilizing said trigger assembly thereby preventing repositioning of said trigger assembly to a pre-actuation orientation.

35. A single use lancet assembly comprising:
   a housing, said housing including an at least partially open interior and a piercing aperture defined therein;
   a lancet, said lancet including a body and a piercing tip;
   said lancet disposed in said open interior of said housing and structured to move at least between a cocked orientation and a piercing orientation;
   a trigger assembly structured to position said lancet into said cocked orientation and to release said lancet from its cocked orientation;
   a driving assembly structured to move said lancet at least temporarily into said piercing orientation; and
   said trigger assembly including a lock member structured to extend into said housing after actuation of said trigger assembly, said lock member structured to be engaged by an actuating mechanism so as to retain said trigger assembly in a post-actuation orientation and prevent re-firing of said lancet.

* * * * *